United States Patent [19]

Khanna et al.

[11] Patent Number: 5,347,000
[45] Date of Patent: Sep. 13, 1994

[54] PROCESS FOR THE PREPARATION OF 2-CHLOROSULFINYLAZETIDINONE

[75] Inventors: Jag M. Khanna; Yatendra Kumar; Arun Malhotra, all of New Delhi, India

[73] Assignee: Ranbaxy Laboratories Ltd., New Delhi, India

[21] Appl. No.: 51,086

[22] Filed: Apr. 21, 1993

[30] Foreign Application Priority Data

Nov. 5, 1992 [IN] India ................... 1014/92

[51] Int. Cl.$^5$ ................ C07D 205/095; C07D 501/02
[52] U.S. Cl. ................................ 540/218; 540/359
[58] Field of Search ................... 540/218, 359

[56] References Cited

U.S. PATENT DOCUMENTS

| | | | |
|---|---|---|---|
| 4,052,387 | 10/1977 | Kukolja | 540/359 |
| 4,075,203 | 2/1978 | Chou | 540/359 |
| 4,081,440 | 3/1978 | Kukolja | 540/359 |
| 4,165,315 | 8/1979 | Kukolja | 540/359 |
| 4,165,316 | 8/1979 | Chou | 540/359 |
| 4,289,695 | 9/1981 | Chou | 540/359 |
| 5,053,501 | 10/1991 | Kapur | 540/359 |
| 5,070,195 | 12/1991 | Khanna et al. | 540/359 |

*Primary Examiner*—Mark L. Berch
*Attorney, Agent, or Firm*—Meltzer, Lippe, Goldstein, Wolf, Schlissel & Sazer

[57] ABSTRACT

A process for preparing a 2-chlorosulfinylazetidinone comprises heating in an inert organic solvent a penicillin sulfoxide ester, at a temperature between about 75° C. and 140° C., with an N-chlorohalogenating agent in the presence of a weakly basic N-alkali metal salt of a cyclic imide. The weakly basic N-alkali metal salt of a cyclic imide acts as an acid scavenger to bind the hydrogen chloride which is produced as a byproduct of the reaction. Preferably, the N-chlorohalogenating agent is N-chlorosuccinimide or N-chlorophthalimide, and the weakly basic N-alkali metal salt of a cyclic imide is the sodium or potassium salt of succinimide or phthalimide.

10 Claims, No Drawings

PROCESS FOR THE PREPARATION OF 2-CHLOROSULFINYLAZETIDINONE

BACKGROUND OF THE INVENTION

The 2-chlorosulfinylazetidine-4-one compounds are valuable intermediates in the preparation of 3-exomethylene compounds which in turn are used in the manufacture of clinically useful antibacterial agents such as Cefaclor, Cefroxidine, etc. These intermediate compounds are conventionally prepared by the reaction of corresponding penicillin sulfoxide esters with N-chlorophthalimide in an inert organic solvent at 75°–140° C.

U.S. Pat. Nos. 4,052,387 (Oct. 4, 1977) and 4,081,440 (Nov. 28, 1978) by Kukolja describe a process for the preparation of 2-chlorosulfinylazetidine-4-one by treatment of the corresponding penicillin sulfoxide ester with an N-chlorohalogenating agent in an inert organic solvent in the presence or absence of a non-alkaline acid scavenger such as propylene oxide, butylene oxide, and the like, to remove any hydrogen chloride formed in the reaction. Cyclization of the intermediate with a Friedel-Craft's catalyst affords the corresponding 3-exomethylene cepham sulfoxide ester in an overall yield of 25–40% (with the exception of example 8 in U.S. Pat. No. 4,052,387).

Further, in U.S. Pat. No. 4,165,315 (Aug. 21, 1979), Kukolja describes a method similar to that of U.S. Pat. Nos. 4,052,387 and 4,081,440 for the preparation of 2-chlorosulfinyl-azetidine-4-one, by using a non-alkaline acid scavenger such as propylene oxide, which on cyclization with stannic chloride gives the 3-exomethylene compound in a very low yield (9–34%).

The methods described in the above patents do not provide an economical, commercially viable process when the reaction scale is increased beyond typical research quantities. For example, in those instances where a quantity of 50 gm or more of penicillin sulfoxide ester has been used as the starting material, the results are poor.

In U.S. Pat. Nos. 4,075,203 (Feb. 21, 1978) 4,165,316 (Aug. 27, 1979) Chou describes an improved process for the preparation of 2-chlorosulfinyl-azetidine-4-one intermediate by carrying out the reaction of penicillin sulfoxide ester with an N-chlorohalogenating agent in the presence of alkylene oxide in combination with calcium oxide as a hydrogen chloride acceptor. The intermediate on cyclization with a Lewis acid affords 3-exomethylene cepham ester with an overall yield varying between 32–59%.

Further improvement is reported in U.S. Pat. No. 4,289,695 (Sep. 15, 1981) by Chou wherein the use of a weakly basic, organic solvent insoluble, poly-4-(vinyl-pyridine) polymer cross linked with divinyl benzene as a hydrogen chloride binding agent has been used in the chlorinating step to give 2-chlorosulfinylazetidine-4-one which on cyclization with a Lewis acid gives the corresponding 3-exomethylene cepham sulfoxide esters.

A further improvement is reported in Indian Patent Application No. 1019/Del/89 (corresponding to U.S. Pat. No. 5,070,195) in which the use of a strongly basic ion exchange resin is described to scavenge liberated hydrogen chloride during the chlorinating step. The 2-chlorosulfinylazetidine-4-one produced by this method is cyclized using a Friedel-Craft's catalyst to afford 3-exomethylene cepham sulfoxide esters.

The present invention relates to an improved method for the preparation of 2-chlorosulfinylazetidine-4-one from penicillin sulfoxide ester. It relates to an improvement in the first step of a two step process for converting penicillin sulfoxide esters via 2-chlorosulfinylazetidine-4-one intermediates to 3-exomethylene sulfoxide esters.

According to this invention, it has been found that a substantially higher yield and purity of 3-exomethylene sulfoxide ester may be achieved when an inert, organic solvent insoluble, weakly basic N-alkali metal salt of cyclic imide is used to bind the hydrogen chloride formed in one of the side reactions during the first stage of the two step process, which first stage comprises the heating of a penicillin sulfoxide ester with an N-halogenating agent in an inert organic solvent at a temperature of about 75° C. to 140° C. to form 2-chlorosulfinyl-azetidine-4-one intermediate.

The use of these weakly basic N-alkali metal salt of cyclic imides effectively removes the hydrogen chloride from the reaction system and thus prevents the formation of degradation products, hence giving overall higher yields. At the end of the reaction, the insoluble inorganic salt of alkali metal and cyclic imide formed during the reaction of hydrogen chloride with weakly basic N-alkali salt of cyclic imide can be easily removed by filtration after cooling the reaction mixture to a desirable temperature.

An advantage of the present invention is that the weakly basic N-alkali metal salts of cyclic imide are inexpensive and can be easily prepared by known methods as compared to the expensive and troublesome methods of preparation of cross-linked polymers as reported in the prior art (e.g., U.S. Pat. No. 4,289,695 of Sep. 15, 1981), thus making the present invention more useful and simpler for industrial preparation.

SUMMARY OF THE INVENTION

In accordance with the present invention, an improved method for the preparation of a 2-chlorosulfinylazetidine-4-one of the formula (II), as shown in the accompanying Table 1, comprises heating in an inert organic solvent a penicillin sulfoxide ester of the formula (I) at a temperature between 75°–140° C. with an N-chlorohalogenating agent and in the presence of an organic solvent insoluble, weakly basic N-alkali metal salt of a cyclic imide. In the inventive process, R is hydrogen, $C_1$–$C_3$ alkyl, halomethyl or cyanomethyl, or R is the group $R_3$, wherein $R_3$ is phenyl, phenyl substituted by $C_1$–$C_4$ alkyl, $C_1$–$C_4$ alkoxy, halo, protected hydroxy, nitro, cyano, or trifluoromethyl, or R is a group of formula (IV) as shown in Table 1, wherein $R_4$ is t-butyl, 2,2,2-trichloroethyl, benzyl or substituted benzyl, or R is a group of formula (VII) as shown in Table 1 wherein $R_5$ has the same meaning as $R_3$ defined above, 1,4-cyanohexadienyl, 2-thienyl, 3-thienyl, 2-furyl, 3-furyl, and n is 0 or 1, or R is substituted aryl, alkyl group of the formula (VIII) as shown in Table 1 wherein $R_6$ is the same as $R_5$ and W is protected hydroxy or protected amino, and $R_1$ is a carboxylic acid protecting group selected from the group consisting of $C_1$–$C_4$ alkyl, 2,2,2-trihaloalkyl, benzyl, substituted benzyl, phenyl halo, substituted phenacyl and benzhydral.

In a preferred embodiment, the weakly basic N-alkali metal salt of cyclic imide comprises N-potassium phthalimide, and the N-chlorohalogenating agent is N-chlorophthalimide or N-chlorosuccinimide.

DETAILED DESCRIPTION OF THE INVENTION

According to the process of this invention, 6-acylamino-2,2-dimethylpenam-3-carboxylic acid ester sulfoxide (I) is reacted with an N-chlorohalogenating agent in the presence of a weakly basic N-alkali metal salt of cyclic imide at a temperature between 75°–140° C. preferably between 100°–135° C., in an inert organic solvent under anhydrous conditions to form the corresponding substituted 2-chlorosulfinylazetidine-4-one represented by the formula (II). Friedel Craft's cyclization of the azetidinone intermediate (II) affords the corresponding 3-exomethylene compound in 65–85% yield.

Acid scavengers used to bind hydrogen chloride in the process of the present invention are weakly basic N-alkali metal salts of cyclic imides. They are insoluble in inert organic solvents under anhydrous conditions and effectively bind hydrogen chloride as shown by eq. 1 below:

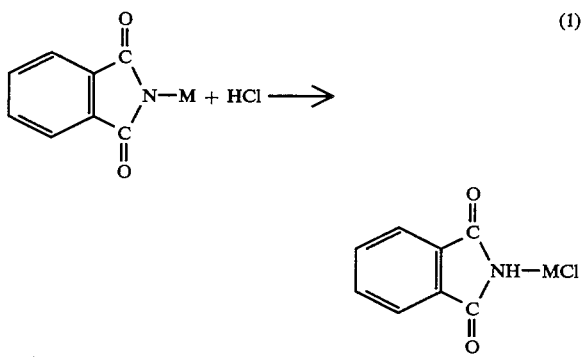

(1)

Cyclic imide and alkali metal chloride formed by the reaction of hydrogen chloride with N-alkali metal salt of cyclic imide are insoluble in inert organic solvent and can be removed by filtration techniques.

The weakly basic N-alkali metal salts of cyclic imides of the formula (XV) as shown in Table 1 used in the process of the present invention are alkali metal salts of cyclic imides wherein Y is O-phenylene or —(CH$_2$)$_n$— in which n is 2 or 3, and M is a metal atom, e.g., sodium and potassium salts of succinimide, phthalimide, etc. They can be easily prepared by known methods in which a solution of equimolar amounts of an alkali metal hydroxide is reacted with cyclic organic imide in an inert solvent, for example, alcohol or a mixture of alcohol with water, or in benzene at reflux temperature and the water generated during the reaction is removed azeotropically. The product thus obtained is washed thoroughly to remove the last traces of unreacted metal hydroxide and can be used directly without further purification in the process of the present invention.

The amount of N-alkali metal salt of cyclic imide used in the process of the present invention is not very critical. Generally, about 0.2 mols/mol of penicillin sulfoxide ester can be employed without compromising the yield of the 3-exomethylene sulfoxide ester (III). However, preferably an amount equal to 0.3 mols/mol of penicillin sulfoxide ester to 0.5 mols/mol of penicillin sulfoxide ester, and more preferably 0.4 mols/mol of penicillin sulfoxide ester, are used in the process of the present invention.

Improved yields of 3-exomethylene sulfoxide ester, compound (III), obtained in the present invention can be attributed to the effective removal of hydrogen chloride by the N-alkali metal salt of cyclic imide, thus preventing the formation of side products. Unreacted N-alkali metal salt of cyclic imide and the byproducts alkali metal chloride and cyclic imide formed by the reaction of hydrogen chloride with the N-alkali metal salt of cyclic imide are insoluble in the organic solvents and can be easily removed by simple filtration.

R$_1$ in the formula (II) as shown in Table 1 denotes a carboxylic acid protecting group. Specific illustrations of the carboxylic acid protecting groups of the sulfinyl chloride of this invention include methyl, ethyl, n-propyl, isopropyl, n-butyl, iso-butyl, sec-butyl, t-butyl, 2,2,2-trichloroethyl, 2,2,2-tribromoethyl, benzyl, p-nitrobenzyl, p-methoxybenzyl, benzhydral, phenacyl, p-chlorophenacyl, p-bromophenacyl, and the like. Highly preferred carboxylic acid protecting groups are methyl, benzyl, p-nitrobenzyl, p-methoxybenzyl, benzhydral and 2,2,2-trichloroethyl.

R in the formula (II) as shown in Table 1 is the residue of the carboxylic acid such as hydrogen, C$_1$–C$_3$ alkyl, cyanomethyl, or halomethyl, or R is the group R$_3$ in which R$_3$ is phenyl or phenyl substituted by C$_1$–C$_4$ alkyl, C$_1$–C$_4$ alkoxy, halo, protected hydroxy, nitro, cyano, or trifluoromethyl, or R is a group of formula (IV) as shown in Table 1 wherein R$_4$ is t-butyl, 2,2,2-trichloroethyl, benzyl, or substituted benzyl, or R is a group of formula (VII) as shown in Table 1 wherein R$_5$ has the same meaning as R$_3$ defined above, 1,4-cyanohexadienyl, 2-thienyl, 3-thienyl, 2-furyl, 3-furyl, and n is 0 or 1, or R is substituted aryl, alkyl group of the formula (VIII) as shown in Table 1 wherein R$_6$ is the same as R$_5$ and W is protected hydroxy or protected amino.

By the term N-chlorohalogenating agent is meant a reagent having at least one chlorine bonded directly to the nitrogen atom with the remaining moiety or moieties of the structure of the reagent having a strong electron withdrawing effect. The by-product corresponding to the N-chlorohalogenating agent after the chlorine atom has been replaced by a hydrogen atom is essentially inert to the sulfinyl chloride product. Several types of N-chlorohalogenating compounds described above include, formula (IX) as shown in Table 1, wherein R$_7$ is hydrogen, chloro, C$_1$–C$_4$ alkyl, cyclohexyl, phenyl, or phenyl substituted with chloro, bromo, methyl or nitro, and R$_8$ is C$_1$–C$_4$ alkyl, cyclohexyl, phenyl, or phenyl substituted with chloro, methyl or nitro, or formula (X) as shown in Table 1 in which R$_7$ and R$_8$ are as defined above, or N-chlorourethane, formula (XI) as shown in Table 1, wherein R$_7$ and R$_8$ are as defined above, or N-chlorosulfanamide, formula (XII) as shown in Table 1, wherein R$_7$ and R$_8$ are as defined above, or N-chlorosulfinanamide, formula (XIII) as shown in Table 1, wherein Y is O-phenylene, or —(CH$_2$)$_n$— in which n is 2 or 3, or N-chloroimide, formula (XIV) as shown in Table 1, wherein Y is the same as defined above.

N-chlorohalogenating agents which are preferred for use in the process of this invention are N-chloroimides, particularly N-chlorosuccinimide and N-chlorophthalimide.

The inert organic solvent in the present process refers to an aprotic organic solvent which does not react appreciably either with the N-chlorohalogenating agent or the 2-chlorosulfinyl-azetidine-4-one (II). Suitable inert organic solvents are those having a boiling point at least as high as the temperature of the reaction and include the aromatic hydrocarbons, such as, benzene, toluene, xylene, ethylbenzene, cumene, tatrialin and the like, halogenated hydrocarbons such as carbon tetrachloride, chloroform, dichloroethane, 1,1,2-trichloroethane, ethylene dibromide, monochlorobenzene, and aromatic ethers such as anisole, diphenyl ether and the like. Preferred organic solvents of this process are benzene, toluene and xylene. Reagent grade solvents are preferably used and suitably dried.

According to the present invention, the reaction of penicillin sulfoxide ester (I) with N-chlorohalogenating agent in the presence of a weakly basic N-alkali metal salt of cyclic imide in a suitable inert organic solvent at 75°–140° C. is carried out to produce the corresponding 2-chlorosulfinylazetidine-4-one (II). Generally from about 1 mole to 1.6 moles of the halogenating agent is used per 1 mole of starting material. The ratio of weakly basic N-alkali metal salt of cyclic imide to penicillin sulfoxide ester (I) ranges between 1.5:1 to 0.2:1.0 mol, the preferred range being 0.4:1 mol.

EXAMPLE 1

Preparation of N-potassium phthalimide

In a 1-liter three-neck round bottom flask, phthalimide (50 g) was suspended in ethyl alcohol (500 ml) and cooled to about 0° C. under stirring. A solution of alcoholic KOH (19 gm in 150 ml alcohol) was added slowly over a period of 15–20 mins., while keeping the mass temperature at 0°–5° C. After the addition was complete, the reaction mixture was stirred for ½ hour at 0°–5° C. and then filtered.

Precipitate thus obtained was a slurry which was washed with alcohol and dried under vacuum to constant weight.

Yield=46.0 gm; m.p.>300°

EXAMPLE 2 p-Nitrobenzyl-3-methyl-2-(2-chlorosulfinyl)-4-oxo-3-phenoxy acetamido-1-azetidinyl-3-Butenoate In a 500 ml 3-necked round bottom flask, 300 ml toluene was dried azeotropically with the help of a Dean and Stark apparatus. The heat was removed and 10 g p-nitrobenzyl-6-phenoxy acetamido-2,2-dimethylpenam-3-carboxylate-1-oxide, 5 gm N-chlorophthalimide and 1.5 g N-potassium phthalimide were added. The reaction mixture was heated at reflux temperature for 100 mins. and then cooled to −10° C. The insoluble material was filtered and the filtrate was concentrated to dryness to provide 10.13 g (95%) of the title compound.

IR(CHCl$_3$) in cm$^{-1}$: 1790, 1750, 1700, 1530, 1350, 1220, 1040.

$^1$HNMR (CDCl$_3$) δ1.90(s,3H) , 4.53(s,2H), 5.13(m,3H) , 5.3(s,2H), 5.55(d,1H), 6.05(dd,1H) and 6.6–8.05(m,9H).

EXAMPLE 3 p-Nitrobenzyl-7-phenoxyacetamido-3-exomethylene cephem-4-carboxylate-1-oxide.

In a 1-liter three-neck round bottom flask, 400 ml of solvent grade toluene was dried azeotropically by removing water with the help of a Dean and Stark apparatus. The solvent was cooled to 50° C. and 20 gm p-nitrobenzyl-6-phenoxyacetamido-2,2-dimethyl penam-3-carboxylate-1-oxide, 10.2 g N-chlorophthalimide and 3.0 g N-potassium phthalimide were added. The reaction mixture was heated to 108°–110° C. for 100 mins. After completion of the reaction, the mixture was cooled to −10° C., stirred for ½ hour, and the insoluble material was filtered.

In another flask a solution of 7.6 ml stannic chloride in 80 ml anhydrous toluene was cooled to 0° C. To this, 4 ml ether were added and slowly the above prepared solution of sulfinyl chloride was added to it, keeping the mass temperature between 0°–5° C. After the addition was complete, the reaction mixture was stirred at 10°–15° C. for 6 hrs. The orange colored complex thus formed was filtered, washed with 100 ml hexane and dried. Stirring of complex in 60 ml methanol at 0°–5° C. gave an off-white product which was further stirred for 2 hrs. at 0°–5° C., filtered, washed with DM water to make the pH neutral, and dried.

Yield=16.9 g (84.5%); m.p.=192°–194° C.

$^1$HNMR (CDCl$_3$) δ3.6(q,2H) , 4.5(S,2H), 4.83(d, 1H) , 5.3(S,2H), 5.33(S,1H), 5.5(S,1H), 5.78(S,1H), 6.02(dd,1H) and 6.9–8.3(m,9H).

Anal. Calcd. CHN for C$_{23}$H$_{21}$N$_3$O$_4$S, C=55.31, H=4.24, N=8.41%. Found C=55.40, H=4.12, N=8.44%.

EXAMPLE 4 p-Nitrobenzyl-7-phenoxyacetamido-3-exomethylene cephem-4-carboxylate-1-oxide 600 ml reagent grade toluene was dried azeotropically in a 1-liter 3-neck round bottom flask by removing water with the help of a Dean and Stark trap. The solvent was cooled to 50° C. and 20 gm of p-nitrobenzyl-6-phenoxyacetamido-2,2'-dimethyl penam 3-carboxylate-1-oxide, 10.2 g N-chlorophthalimide and 0.3 g N-potassium phthalimide were added in one lot. The suspension was heated at reflux temperature for 110 mins. and was then cooled to −10° C., and kept ½ hr at this temperature. The solids thus separated were filtered and the filtrate was cooled to 0° C. Diethyl ether (4 ml) was added to cold filtrate and a solution of 7.5 ml stannic chloride in 10 ml toluene was then slowly added keeping mass temperature between 0°–5° C. Resulting orange complex was further stirred at 10°–15° C. for 6 hrs, filtered and washed with hexane. The complex thus obtained was slowly added to 60 ml methyl alcohol with stirring. The off-white precipitate of the product thus obtained was stirred for 2 hrs at 0°–5° C., filtered, washed with methyl alcohol and made to neutral pH by DM water washings. The product was then dried in vacuum at 40°–45° C. to constant weight.

Yield=13 g (70%); m.p.=196°–198° C.

EXAMPLE 5 p-Nitrobenzyl-7-phenylacetamido-3-exomethylene cephem-4-carboxylate-1-oxide

In a 1-liter three-neck round bottom flask, 400 ml reagent grade toluene was azeotropically dried by removing moisture with the help of a Dean and Stark trap. Solvent was cooled to 50° and 19.4 g p-nitrobenzyl-6-phenylacetamido-2,2'-dimethyl penam-3-carboxylate-1-oxide, 10.1 g N-chlorophthalimide and 3.0 g N-potassium phthalimide were added. Suspension was heated at reflux temperature for 110 mins., then cooled to −5° C. and filtered.

In another flask, 80 ml anhydrous toluene and 7.6 ml stannic chloride were cooled to 0° C. To this, 4 ml ether were added and the above prepared sulfinyl chloride was slowly dropped into this mixture keeping mass temperature at 0°-5° C. The orange-red complex thus obtained was further stirred at 10°-15° C. for 8 hrs, filtered, washed with hexane and decomposed by slowly adding it to 60 ml methyl alcohol. The product thus obtained was stirred at 0°-5° C. for 2 hrs., filtered, washed with 40 ml methyl alcohol and vacuum dried to give 12.6 g (65%) of the title compound.

M.p.=206°-208° C.

$^1$HNMR (CDCl$_2$) δ 3.3-3.8 (m,4H), 5.3 (d,1H), 5.25(S,3H), 5.45(S,1H), 5.75 (S,1H), 6.0 (dd,1H), 6.9(d,1H), and 7.2-8(m,9H).

EXAMPLE 6 p-Nitrobenzyl-7-phenoxyacetamido-3-exomethylene cepham-4-carboxylate-1-oxide

In a 500 ml 3-neck round bottom flask, reagent grade toluene was dried azeotropically with the help of a Dean and Stark apparatus by removing moisture. Heat was removed and the mass was cooled to 50° C. 10 g of p-nitrobenzyl-6-phenoxyacetamido-2,2'-dimethyl penam-3-carboxylate-1-oxide, 5.0 g N-chlorophthalimide and 1.68 g N-sodium phthalimide weree added in one lot. The mass was heated to 108°-110° C. for 100 mins. After the complete disappearance of starting material on TLC, the mass was cooled to −5° C. and held at this temperature for 15 mins. and filtered.

In another flask, 3.8 ml of stannic chloride in 40 ml toluene was cooled to 0° C. To this cooled mixture, 2 ml ether was added and slowly above prepared sulfinyl chloride was dropped into it keeping mass temperature between 0°-5° C. Resulting buff-colored complex was stirred at 10°-15° C. for 6 hrs., filtered and washed with 25 ml hexane. Product was obtained by slowing adding this complex to 30 ml methyl alcohol at 0°-5° C. and further stirring the off-white crystalline product at 0°-5° C. for 2 hrs. The product was filtered and washed with methanol and made to neutral pH by repeated DM water washings. Finally, the product was dried in vacuum at 40°-45° C. to constant weight.

Yield=8 gm (80%); mp=193°-195° C.

EXAMPLE 7 p-Nitrobenzyl-7-phenoxyacetamido-3-exomethylene cepham-4-carboxylate-1-oxide

In a 1-liter 3-neck round bottom flask, 600 ml reagent grade toluene was dried azeotropically using a Dean and Stark water trap. Heat was removed and 10 gm of p-nitrobenzyl-6-phenoxyacetamido-2,2'-dimethyl penam-3-carboxylate-1-oxide, 5.1 gm N-chlorophthalimide and 1.36 gm N-potassium succinimide were added. The mass was heated to 108°-110° C. and progress of the reaction was monitored by TLC. After 100 mins., when all the starting material was consumed, the mass was cooled to 0° C., stirred for 15 mins., and filtered to remove solids. To this filtrate, 2 ml ether was added and 3.8 ml stannic chloride was slowly added keeping the temperature 0°-5° C. The thick complex thus obtained was further stirred at 10°-15° C. for 6 hrs, filtered, washed with hexane, and hydrolysed by adding it slowly to 30 ml methanol at 0°-5° C. The product thus obtained was further stirred at 0°-5° C. for 2 hrs and worked up to give 7.5 g (75%) of the title compound.

EXAMPLE-8

2,2,2-Trichloroethyl-3-methyl-2-[2-chlorosulfinyl-4-oxo-3-phenoxyacetamido-1-azetedinyl]-3-Butanoate To 300 ml of anhydrous toluene in a 500 ml three-necked round bottom flask, 9.95 g of 2,2,2-trichloroethyl-6-phenoxyacetamido-2,2'-dimethyl penam-3-carboxylate-1-oxide, 5.1 g N-chlorophthalimide and 1.5 g N-potassium phthalimide were added. The suspension was heated to 108°-110° C. for 100 mins, cooled to −10° C. and filtered. The filtrate was evaporated to dryness to provide 96% of title product.

EXAMPLE 9

2,2,2-Trichloroethyl-7-phenoxyacetamido-3-exomethylene cephem-4-carboxylate-1-oxide In a 500 ml 3-necked round bottom flask, 300 ml of toluene was azeotropically dried by removing moisture with the help of a Dean and Stark apparatus. Heat was removed and 9.95 g of 2,2,2-trichloroethyl-6-phenoxyacetamido-2,2'-dimethyl penam-3-carboxylate-1-oxide, 5.1 g N-chlorophthalimide and 1.5 g N-potassium phthalimide were added. The suspension was heated to 108°-110° C. for 100 mins. after cooling the reaction mixture to −10° C. The solids were filtered off.

In another flask, 3.8 ml of stannic chloride in 40 ml toluene were cooled to 0° C., and 2.0 ml of ether were then added. To this mixture, the above prepared solution of sulfinyl chloride was added slowly keeping mass temperature between 0°-5° C. The orange colored complex thus obtained was then stirred for 6 hrs. at 10°-15° C., filtered, washed with hexane, and decomposed by adding slowly to 30 ml methyl alcohol at 5°-10° C. Off-white product thus obtained was further stirred at 0°-5° C. for 2 hrs, and worked up to give 6.95 g (70%) of the title compound. M.P.=141°-143° C.

While the invention has been described by reference to specific examples, this was for purposes of illustration only. Numerous alternative embodiments will be apparent to those skilled in the art and are considered to be within the scope of the invention.

TABLE 1

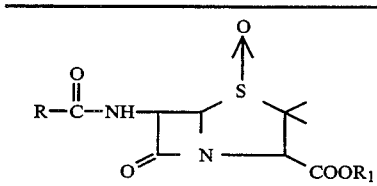

FORMULA I

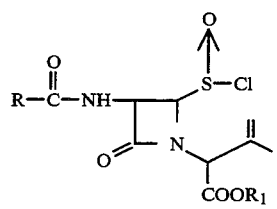

FORMULA II

TABLE 1-continued

FORMULA III: R—C(=O)—NH— attached to β-lactam with S→O, =CH2, COOR1

FORMULA IV: R4—O—

FORMULA VII: R5—(O)n—CH2—

FORMULA VIII: R6—CH(W)—

FORMULA IX: Cl—N(R7)—C(=O)—N(R8)—Cl

FORMULA X: R7—C(=O)—N(R8)—Cl

FORMULA XI: R7—O—C(=O)—N(R8)—Cl

FORMULA XII: R7—SO2—N(R8)—Cl

FORMULA XIII: cyclic Y—C(=O)—N(Cl)—S(O2)—

FORMULA XIV: cyclic Y with two C=O and N—Cl

FORMULA XV: cyclic Y with two C=O and N—M

We claim:

1. A process for preparing a 2-chlorosulfinylazetidinone of the formula (II),

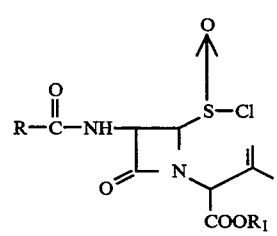

FORMULA II wherein

R is hydrogen, $C_1$–$C_3$ alkyl, halomethyl or cyanomethyl, or

R is the group $R_3$, wherein $R_3$ is phenyl or phenyl substituted by $C_1$–$C_4$ alkyl, $C_1$–$C_4$ alkoxy, halo, protected hydroxy, nitro, cyano, or trifluoromethyl, or R is a group of formula (IV), $$R_4\text{—O—} \qquad \text{FORMULA IV}$$

wherein $R_4$ is t-butyl, 2,2,2-trichloroethyl, benzyl, or

R is a group of formula (VII), $$R_5\text{—(O)}_n\text{—CH}_2\text{—} \qquad \text{FORMULA VII}$$

wherein $R_5$ is as $R_3$ defined above, 2-thienyl, 3-thienyl, 2-furyl, or 3-furyl, and n is 0 or 1, or R is a substituted aralkyl group of formula (VIII), $$R_6\text{—CH—} \atop W \qquad \text{FORMULA VIII}$$

wherein $R_6$ has the same meaning as $R_5$ defined above, and W is protected hydroxy or protected amino, and $R_1$ is a carboxylic acid protecting group selected from the group consisting of $C_1$–$C_4$ alkyl, 2,2,2-trihaloalkyl, benzyl, p-nitrobenzyl, p-methoxybenzyl, phenacyl, halo substituted phenacyl and 1,1 diphenylmethyl, which process comprises heating in an inert organic solvent a penicillin sulfoxide ester of the formula (I), FORMULA I: R—C(=O)—NH— penicillin sulfoxide ester with COOR1 wherein R and $R_1$ are as defined above, at a temperature between about 75° and 140° C., with an N-chlorohalogenating agent and in the presence of a weakly basic N-alkali metal salt of phthalimide or succinimide.

2. The process of claim 1 wherein said weakly basic N-alkali metal salt of a cyclic imide comprises a sodium or potassium salt of phthalimide or succinimide.

3. The process of claim 1, wherein R is benzyl or phenoxymethyl and $R_1$ is benzyl, p-nitrobenzyl, p-methoxybenzyl, 1,1 diphenylmethyl or 2,2,2-trihaloethyl.

4. The process of claim 1, wherein said N-chlorohalogenating agent is selected from the group consisting of N-chlorourea, N-chloroamide, N-chlorourethane, N-chlorosulfamide, N-chlorosulfimide and N-chloroimide, as shown in the formulas (XI)–(XIV) below FORMULA IX: Cl—N(R7)—C(=O)—N(R8)—Cl -continued

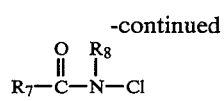
FORMULA X

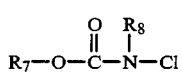
FORMULA XI

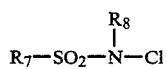
FORMULA XII

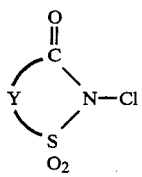
FORMULA XIII

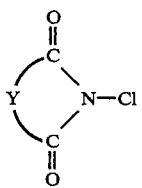
FORMULA XIV wherein
$R_7$ is hydrogen, chloro, $C_1$–$C_4$ alkyl, cyclohexyl, phenyl, or phenyl substituted with chloro, bromo, methyl or nitro, $R_8$ is $C_1$–$C_4$ alkyl, cyclohexyl, phenyl, or phenyl substituted with chloro, bromo, methyl or nitro, and Y is O-phenylene or —$(CH_2)_n$— in which n is 2 or 3.

5. The process of claim 1 wherein the weakly basic N-alkali metal salt of phthalimide or succinimide has the structure of formula (XV),

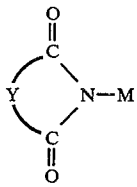
FORMULA XV wherein Y is O-phenylene, or —$(CH_2)_n$— in which n is 2, and M is sodium or potassium.

6. The process of claim 1, wherein said N-chlorohalogenating agent is N-chlorosuccinimide or N-chlorophthalimide.

7. The process of claim 1, wherein said inert organic solvent is an aromatic organic solvent selected from the group consisting of benzene, toluene, xylene and halogenated aliphatic hydrocarbons.

8. A process for preparing a 3-exomethylene sulfoxide ester which comprises preparing a 2-chlorosulfinylazetidinone of formula (II) in accordance with claim 1, and cyclizing the 2-chlorosulfinylazetidone.

9. The process of claim 8 wherein said 2-chlorosulfinylazetidone is cyclized in the presence of a Friedel-Craft's catalyst.

10. The process of claim 9 wherein said Friedel-Craft's catalyst is stannic chloride.

* * * * *